(12) United States Patent
Abshear et al.

(10) Patent No.: US 7,705,854 B2
(45) Date of Patent: *Apr. 27, 2010

(54) OVERLAP DENSITY (OD) HEATMAPS AND CONSENSUS DATA DISPLAYS

(75) Inventors: Ty Abshear, Grand Junction, CO (US); Gregory M. Banik, Moorestown, NJ (US); Karl Nedwed, Graz (AT)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/337,530

(22) Filed: Dec. 17, 2008

(65) Prior Publication Data

US 2009/0096791 A1    Apr. 16, 2009

Related U.S. Application Data (63) Continuation of application No. 11/360,000, filed on Feb. 21, 2006, now Pat. No. 7,492,372.

(51) Int. Cl.
  *G09G 5/00*    (2006.01)
  *G09G 5/02*    (2006.01)
  *G06T 11/20*   (2006.01)

(52) U.S. Cl. .................. 345/581; 345/586; 345/606; 345/619; 345/440; 382/168; 382/207; 382/300

(58) Field of Classification Search ............... 345/581, 345/419, 619, 629, 586, 606, 440, 618, 643, 345/653; 382/168–170, 207, 214, 298–300; 702/66–67, 71–74

See application file for complete search history.

(56) References Cited

U.S. PATENT DOCUMENTS

| | | | | |
|---|---|---|---|---|
| 6,334,099 | B1 * | 12/2001 | Grace et al. ................. | 702/194 |
| 7,492,372 | B2 * | 2/2009 | Abshear et al. ............. | 345/581 |
| 2002/0026294 | A1 * | 2/2002 | Grace et al. ................. | 702/190 |
| 2003/0028560 | A1 * | 2/2003 | Kudrolli et al. ............ | 707/509 |
| 2004/0086175 | A1 * | 5/2004 | Parker et al. ................ | 382/154 |
| 2004/0103132 | A1 * | 5/2004 | Zakrzewski ................ | 708/290 |
| 2005/0209789 | A1 * | 9/2005 | Hastings ..................... | 702/22 |

\* cited by examiner

*Primary Examiner*—Wesner Sajous
(74) *Attorney, Agent, or Firm*—Townsend and Townsend and Crew LLP (57) ABSTRACT

Systems and methods that generate or provide overlap displays of multiple sets of data in a manner that advantageously simplifies trend visualization in large sets of data. A two-dimensional, three-dimensional, or greater-dimensional occurrence count array is generated for a plurality of similar data sets. Each element in the array is a number of times a corresponding vector of data values occurs in the plurality of N data sets, wherein each array element corresponds to a discrete interval of data values. Once the array has been generated, a graphical display of overlap density may be generated by comparing a desired degree of overlap with the value of each array element. Those array elements having values that satisfy the desired degree of overlap are rendered, as a display object, using one or more colors, shades and/or patterns representing varying degrees of overlap.

20 Claims, 5 Drawing Sheets

IR Spectra as an OD HEATMAP; OD Level = 0.

FIG. 1 – IR Spectra stacked in a conventional fashion.

FIG. 2

FIG. 3 – Generation of a 4x4 Occurrence Count Array from 2 Data Sets.

FIG. 4 – IR Spectra as an OD HEATMAP; OD Level = 0.

FIG. 5 – IR Spectra as an OD HEATMAP; OD Level = 100.

FIG. 6 – IR Spectra as an OD HEATMAP; OD Level = 50.

FIG. 7 – IR Spectra as an OD CONSENSUS; OD Level = 50.

FIG. 8 - IR Spectra as an OD CONSENSUS; OD Level = -100

OVERLAP DENSITY (OD) HEATMAPS AND CONSENSUS DATA DISPLAYS

This application is a continuation of prior application Ser. No. 11/360,000, filed Feb. 21, 2006, which is hereby incorporated by reference for all purposes.

BACKGROUND OF THE INVENTION

The present invention relates generally to data displays, and more particularly to displays of multiple overlapping sets of data.

In many fields, scientists must make sense of and find patterns in large amounts of data. One example of this is in the field of metabolomics, the study of metabolic changes in response to perturbations, such as a drug or disease. Metabolomics blends statistical analysis with analytical chemistry techniques such as nuclear magnetic resonance (NMR) spectroscopy, mass spectrometry (MS) and chromatography. Predicted to become the center of drug discovery and development, metabolomics may lead to earlier, faster, and more accurate diagnosis for many diseases.

Figure 1:
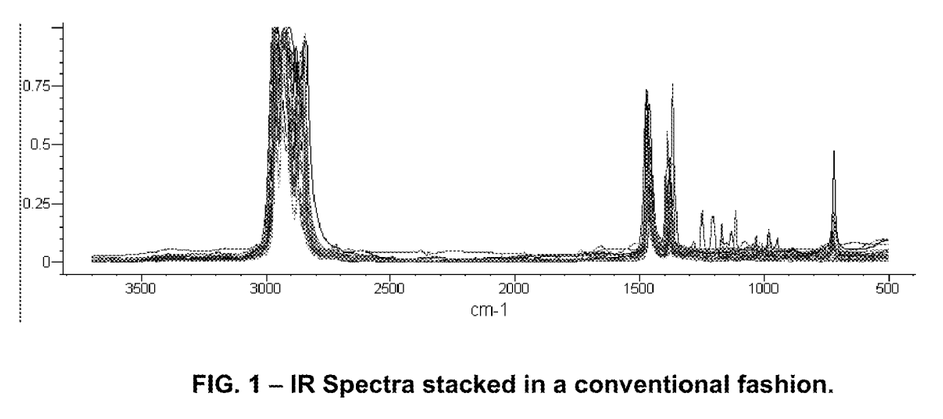
FIG. 1 shows 25 IR spectra, all normal and branched alkanes, in a traditional stacked display.

In general, when displaying large amounts of data simultaneously, it can be very difficult, if not impossible, to visualize trends in the data using traditional display systems. For example, FIG. 1 illustrates an example of a traditional graphical representation of a plurality of IR spectra. Each spectrum is arbitrarily assigned a different unique color. While there is clearly overlap between the different spectra, it is difficult, if not impossible, with this traditional type of stacked data display to visualize the areas of highest overlap among the IR spectra displayed.

Therefore it is desirable to provide systems and methods that overcome the above and other problems. Such systems and methods should provide useful displays of overlapping data, and should allow for flexible manipulation of the data displays to provide enhanced data mining and trend visualization capabilities.

BRIEF SUMMARY OF THE INVENTION

The present invention provides systems and methods that generate or provide overlap displays of multiple sets of data in a manner that advantageously simplifies trend visualization in large sets of data. In general, the present invention is applicable to graphical displays of any type of data that is desired to be displayed. For example, the present invention can be used to analyze large amounts of graphical data from such disciplines as cheminformatics, analytical informatics, metabolomics, chemometrics, genomics, proteomics and others, and has applicability in all branches of scientific research, including life sciences and diagnostics.

According to the present invention, a 2-dimensional occurrence count array is generated for a plurality of similar data sets. The value of each element in the array represents a number of times a corresponding pair of data values x, y occurs in the plurality of N data sets, wherein each array element corresponds to a discrete interval of x and y data values. The occurrence count process, in one aspect, is analogous to laying a 2-dimensional array over a combined display of all the data sets being processed and counting, for each array element, the number of data sets having data within the x-y range of the corresponding array element. Once the array has been generated, a graphical display of overlap density may be generated by comparing a desired percentage of overlap with the value of each array element. Those array elements having values that satisfy the desired percentage of overlap are rendered as a display object. For example, an OD HEATMAP object, representing a particular percentage of overlap or range of overlap percentage, in one aspect, may be displayed as a range of one or more colors, shades, and/or patterns ranging from one particular color, shade, or pattern to denote the region of highest overlap between all N data sets to a second color, shade, or pattern to denote the region of lowest overlap between all data sets with a range of colors, shades, or patterns denoting regions of intermediate overlap.

According to one aspect of the present invention, a method is provided for generating data for displaying a plurality of similar data sets. The method typically includes receiving a plurality of N data sets, each data set including two or more pairs of data values representing quantities x and y, and generating an occurrence count array including X times Y elements, by determining an occurrence count value, M, for each array element, wherein each occurrence count value, M, is a number of times a corresponding pair of data values x, y occurs in the plurality of N data sets, wherein each array element corresponds to a discrete interval of x and y data values. The method also typically includes receiving an indicator of overlap density, said indicator representing identifying a range of data overlap percentage, determining the array elements that are within the identified range of overlap percentage, and generating graphical data for a graphical display representing the elements in the array that are within the identified range of data overlap percentage. In certain aspects, the indicator may identify a data overlap percentage range of between 0% and 100%, wherein the corresponding display represents a union of between 2 and all N data sets. In certain aspects, the indicator may identify a data overlap percentage equal to 100%, wherein the display represents an intersection of all N data sets. In certain aspects, the indicator may identify a data overlap percentage equal to 0%, wherein the display represents a difference of all N data sets, or unique values across all N data sets.

According to another aspect of the present invention, a computer-readable medium is provided that includes code which when executed by a processor controls the processor to generate graphical data for rendering a display of a plurality of similar data sets. The code typically includes instructions to generate an occurrence count array for a plurality of N data sets, each data set including two or more pairs of data values representing quantities x and y, the array including X times Y elements, by determining an occurrence count value, M, for each array element, wherein each occurrence count value, M, is a number of times a corresponding pair of data values x, y occurs in the plurality of N data sets, wherein each array element corresponds to a discrete interval of x and y data values. The code also typically includes instructions to determine the array elements that are within an identified overlap percentage in response to a user input indicator of overlap density, wherein the indicator identifies the data overlap percentage. The code further typically includes instructions to generate graphical data for a graphical display representing the elements in the array that are within the identified data overlap percentage. In certain aspects, the indicator may identify a data overlap percentage range of between 0% and 100%, wherein the corresponding display represents a union of between 2 and all N data sets. In certain aspects, the indicator may identify a data overlap percentage equal to 100%, wherein the display represents an intersection of all N data sets. In certain aspects, the indicator may identify a data overlap percentage equal to 0%, wherein the display represents a difference of all N data sets, or unique values across all N data sets.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers indicate identical or functionally similar elements.

DETAILED DESCRIPTION OF THE INVENTION

The present invention provides systems and methods that generate or provide overlap displays of multiple sets of data in a manner that advantageously simplifies trend visualization in large sets of data. In general, the present invention is applicable to graphical displays of any type of data that is desired to be displayed.

In certain aspects, for example, the present invention is useful for evaluating and discovering trends and commonalities in large data sets including the following graphical object types: Circular Dichroism (CD); Conductometry; Coulometry; Densitograms resulting from gel electrophoresis, etc; Differential Scanning Calorimetry (DSC); Differential Thermal Analysis (DTA); Electron Spin Resonance (ESR); Electropherogram resulting from gel electrophoresis, etc.; Gas Chromatograms (GC); High Performance Liquid Chromatograms (HPLC); Histogram Plots; Infrared (IR) Spectra; Ion Mobility Spectrometry (IMS); Liquid Chromatograms (LC); Mass Spectra (MS); Nuclear Magnetic Resonance (NMR); Optical Rotary Dispersion (ORD); Polarography; Potentiometry; Raman Spectra; Supercritical Fluid (SCF) Chromatograms; Thermogravimetric Analysis (TGA); Ultraviolet-Visible (UV-Vis) Spectra; Voltammetry; X-Ray Fluorescence (XRF) Spectra; X-Ray Powder Diffraction (XRPD); X-Y Line Plots; X-Y Scatter Plots, and others.

In one aspect, the present invention is applicable to processing data sets, where each data set includes a plurality of data points, each having a pair of values representing the quantities of analytical interest. Such a data set can be represented in a two-dimensional coordinate system with one axis representing one quantity of interest and the other axis representing another quantity of interest. For example, in the case of IR spectra, the pair of values might represent the frequency (or wavelength) and the intensity value. FIG. 1 illustrates an example of a traditional graphical representation of a plurality of IR spectra, where the x-axis represents the wavelength value and the y-axis represents the intensity value (normalized). Each spectrum is arbitrarily assigned a different unique color. While there is clearly overlap between the different spectra, it is difficult, if not impossible, with this traditional type of stacked data display to visualize the areas of highest overlap amongst the displayed objects (the displayed IR spectra). As will be discussed below, the techniques of the present invention enable enhanced visualization of the degree of overlap of the graphical objects.

Similarly, in another aspect, the present invention is applicable to processing data sets, where each data set includes a plurality of data points, each having 3 (or more) values representing quantities of analytical interest. Such a data set can be displayed in a 3- (or more) dimensional coordinate system, with each axis representing one of 3 types of data values. Such a data set can also be viewed in a two dimensional coordinate system with two of the 3 (or more) data values being used to define the 2-dimensional coordinate system. Viewing such data sets in a 2-dimensional coordinate system is analogous to taking cross-sectional slices of a 3- (or more) dimensional image. Accordingly, it should be understood that the present invention is applicable to visual displays representing 3 (or more) dimensions. However, for the sake of simplicity, the following discussion will focus on 2-dimensional visual data displays.

Figure 2:
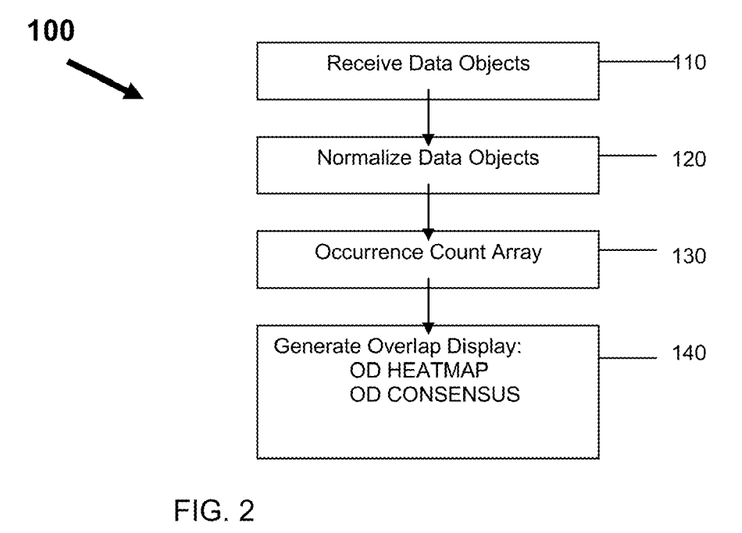
FIG. 2 illustrates the results of a process for generating overlap displays of a plurality of data sets or data objects according to an embodiment of the present invention.

According to the present invention, an embodiment of a process 100 for generating overlap displays of a plurality of data sets or data objects is generally described with reference to FIG. 2. In step 110, a plurality of data sets are received or otherwise acquired. In certain aspects, the data sets should include data that is continuous and equally spaced at discrete intervals along an axis. For example, in FIG. 1, the IR spectra data includes continuous data along the x-axis (wavenumbers) at discrete intervals of approximately 4 $cm^{-1}$.

In the case where process 100 is implemented in an intelligence module (e.g., processor executing instructions) resident in a data acquiring device, such as an IR spectrometer, the data sets may be provided to the intelligence module in real-time as data is being collected, or it may be stored in a memory unit or buffer and provided to the intelligence module after an experiment has been completed. Similarly, the data sets may be provided to a separate system such as a desktop computer system or other computer system, via a network connection (e.g., LAN, VPN, intranet, Internet, etc.) or direct connection (e.g., USB or other direct wired or wireless connection) to the acquiring device, or provided on a portable medium such as a CD, DVD, floppy disk or the like. In certain aspects, the data sets each include data points having at least a pair of values (or a 2-dimensional vector) representing the quantities of analytical interest. For example, in the case of IR spectra the pair of values might represent the frequency (or wavelength) and the intensity value. After the data sets have been received or acquired in step 110, the data sets may be processed.

In step 120, the data sets are optionally normalized. For example, in one aspect, the data sets are normalized to the same x-y resolution. Where all the data sets being processed are provided by the same instrument, this step may not be necessary as all the data sets will likely have the same x-y resolution. However, the x and/or y-values may be normalized by setting the maximal value to an arbitrary value such as 1 or 100, e.g., by dividing the entire data set by the maximal value and multiplying by the arbitrary value. Additionally, it should be understood that the data sets may be normalized before step 110. For example, a separate process or system may normalize the data sets and provide the normalized data sets for processing and generation of the overlap and consensus displays.

In step 130, an occurrence count process is executed. In one aspect, a 2-dimensional array of occurrence counts is generated. In this aspect, each data set is divided into the same x-axis range and the same y-axis range. For example, the x-axis might be broken into 1000 discrete intervals and the y-axis might be broken into 1000 discrete intervals, corresponding to an occurrence count array of dimension 1000× 1000 ($10^6$ array elements) or the x-axis might be broken into 1000 discrete intervals and the y-axis might be broken into 500 discrete intervals, corresponding to an occurrence count array of dimension 1000×500 ($5 \times 10^5$ array elements). In general, the x-axis and y-axis intervals may be the same or they may be different. Also, an occurrence count array may be of any dimension such as having a number of array elements up to $10^6$, $10^8$, $10^{10}$ or greater. The occurrence count process is analogous to laying a 2-dimensional array over a combined display of all the data sets being processed and counting, for each array element, the number of data sets having data within the x-y range of the array element.

Figure 3:
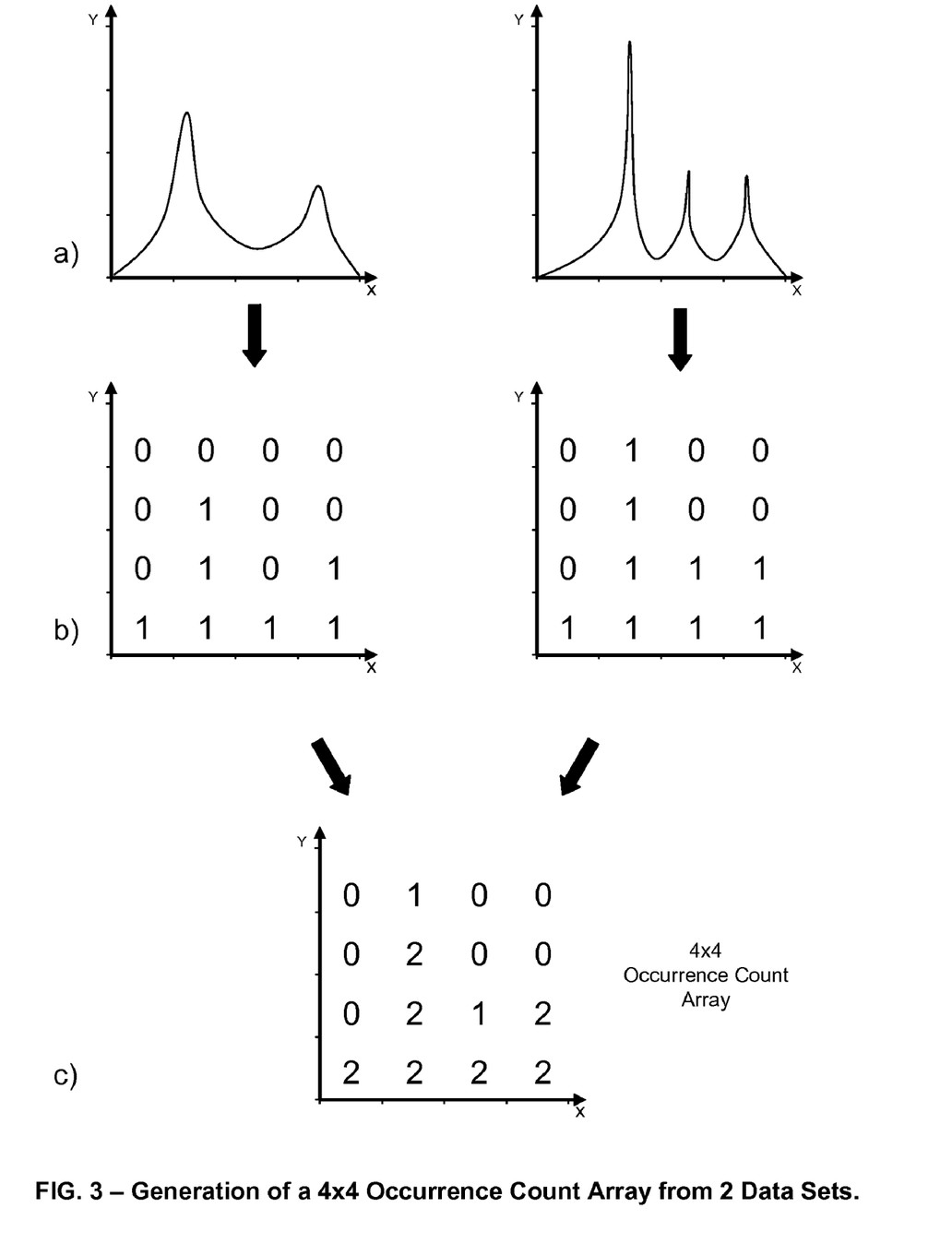
FIG. 3 illustrates a simplified example of generating a 4×4 occurrence count array for two data sets.

FIG. 3 illustrates a simplified example of generating a 4×4 occurrence count array for two data sets. FIG. 3a, shows the two data sets plotted in an x-y coordinate system. As shown, the plots span 4 x-value intervals and 4 y-value intervals for a total of 16 array elements. FIG. 3b illustrates an occurrence count array for each individual data set; in this example, each array element in the 4×4 array is assigned a 1 or a 0 depending on whether the data set includes data within the x-y range of the array element. FIG. 3c illustrates a combined occurrence count array for both data sets. As can be seen, each array element has a value of 0, 1 or 2, depending on whether the data sets include data in the array element range. In one aspect, when generating an occurrence count array, each array element will have a value, M, ranging from 0 to N, the number of data sets to which the occurrence count process is applied. Any array element in the occurrence count array having a value of N represents a data point that is common to all N data sets; similarly an array element having a value of 0 represents a data point included in none of the N data sets. An intermediate value (M=1 to N−1) represents a data point that is common to 1 or more, but not all of the N data sets. The degree of commonality for a specific array element can be determined by dividing the value, M, of the particular array element value by the number, N, of data sets processed:

M/N=degree of commonality.

If M/N=1 then all data sets processed include the data value represented by the array element; there is a complete overlap of all data sets within that x-y data value range represented by the array element. Similarly, if M/N<1 there is less than a complete overlap. If M/N=0 then none of the data sets includes data within the x-y data value range represented by the array element. The maximum M value, $M_{max}$, and therefore also the maximum M/N value for the occurrence count array, $(M/N)_{max}$, is also useful for determining degree of overlap for use in rendering overlap displays as will be discussed more below. Likewise, the minimum M value for the occurrence count array, $(M/N)_{min}$, is also useful for determining degree of overlap.

In certain aspects, interpolated values may be used when generating an occurrence count array. For example, in the case where the data sets include only 500 x-values, for a 1000×1000 occurrence count array, an interpolation process may be implemented (e.g., using a least squares process, a cubic spline interpolation process, etc.), to provide the interpolated data values. Also, a simple average of 2 (or more) data values surrounding an array element may be used.

Returning to FIG. 2, in step 140, an overlap display is generated. In one aspect, a user may select the type of display as well as a degree of overlap to be displayed. Types of displays include overlap density heatmap (OD heatmap) displays and overlap density consensus (OD consensus) displays as will be discussed in more detail below. In this step, a degree of overlap that is desired to be displayed is required as an input parameter. As a default, a parameter indicating complete overlap may be provided. In one aspect, the degree of overlap may be selected by a user using slider 10 as shown in FIGS. 4-9 and discussed in more detail below.

In one aspect, a display of an OD HEATMAP may be rendered on a display device, e.g., a display coupled with the intelligence module that is processing the data sets. As used herein, an OD HEATMAP is an object representing overlapped data objects. An OD HEATMAP, in one aspect, is displayed as a range of colors, shades, and/or patterns ranging from one particular color, shade, or pattern to denote the region of highest overlap between all N data objects (OBJECTS) to a second color, shade, or pattern to denote the region of lowest overlap between all OBJECTS with a range of colors, shades, or patterns denoting regions of intermediate overlap. In general, an "OBJECT" refers to a data set, whether it be a received data set, or a processed data set, e.g., OD HEATMAP OBJECT or OD CONSENSUS OBJECT. Any object can itself be used for later processing, e.g., using an OD CONSENSUS object as a standard for comparison with other data OBJECTS.

An OD HEATMAP can be defined to display all regions of the overlapped OBJECTS that define the union (UNION) of all of the OBJECTS, the regions of the overlapped OBJECTS that are common to all OBJECTS (INTERSECTION), or any range in between the UNION or INTERSECTION defined by the percentage of objects that overlap in each region of the overlapped OBJECTS. In another aspect, an OD HEATMAP can be defined to display regions of the OBJECTS that are unique or different, or which have very little or nothing in common, as will be discussed below.

In one aspect, a numerical OD scale ranging from I to J and from J to K is used to define the OD HEATMAP, where K represents data where 100% of the objects overlap (INTERSECTION; $(M/N)_{max}$) across all N objects, J represents all data (UNION; M/N>0) and an intermediate value between J and K represents some range in between UNION and INTERSECTION. Similarly, I represents data where no objects overlap (UNION MINUS ALL INTERSECTIONS; $(M/N)_{min}$) and an intermediate value between I and J represents something between UNION and (UNION MINUS ALL INTERSECTIONS). I, J and K can be any arbitrary value, such as I=−100, J=0 and K=100.

To determine the colors to be displayed for the OD HEATMAP, in one aspect normalized occurrence count values are determined and matched to the color scale, e.g., by multiplying each array value, M, by (number of colors−1)/$M_{max}$. For example, for 16 colors (4-bit color scale), each array element value is multiplied by 15/$M_{max}$. OD HEATMAP display examples and sample code for determining HEATMAP objects and display colors are presented below. In certain aspects, a user may select the OD scale value and/or color scale used to render a display.

In another aspect, a display of an OD CONSENSUS may be rendered. In one aspect, an OD CONSENSUS is an object that represents the maximal value across all data sets (OBJECTS) at the OD scale value. An OD CONSENSUS may be created, or a user may convert any OD HEATMAP to an OD CONSENSUS, by specifying the amount of overlap density (e.g., on an arbitrary scale of I=INTERSECTION MINUS ALL UNIONS, J=UNION, and K=INTERSECTION on the OD scale) and creating a single OBJECT based on the maximal density value of all OBJECTS at the given OD scale value. The OD CONSENSUS is useable as an OBJECT, e.g., as a standard for comparison with other data OBJECTS. AN OD CONSENSUS display example and sample code for determining CONSENSUS objects are presented below.

Figure 4:
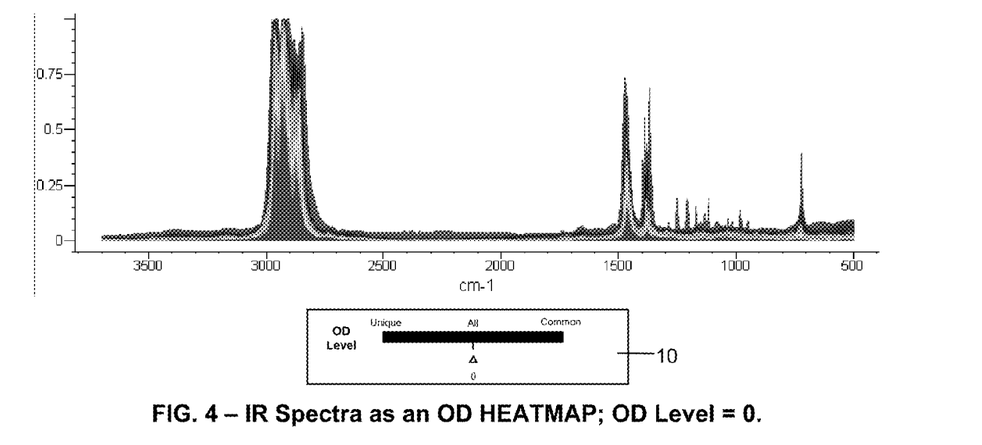
FIG. 4 illustrates a display of the IR spectra shown in FIG. 1 as an OD HEATMAP with the OD Scale value set at 0.

FIGS. 4-8 illustrate examples of OD HEATMAP and OD CONSENSUS displays according to the present invention using an OD scale with I, J and K set to arbitrary values of −100, 0 and 100, respectively. FIG. 4 shows the display of the IR spectra shown in FIG. 1 as an OD HEATMAP with the OD scale value set at 0. With the OD scale value set at 0 (UNION), all areas of the OD HEATMAP are displayed regardless of the overlap density level. In this example, the regions of the spectra representing overlap of 100% of all spectral OBJECTS (OD scale=100) are displayed as red (arbitrarily selected for this example; the color can be user-defined), the regions of the spectra covered by a single spectrum (OD scale=−100) are displayed as violet (arbitrarily selected for this example; the color can be user-defined), and all spectral regions representing intermediate levels of overlap density are represented by colors ranging from red through violet.

Figure 5:
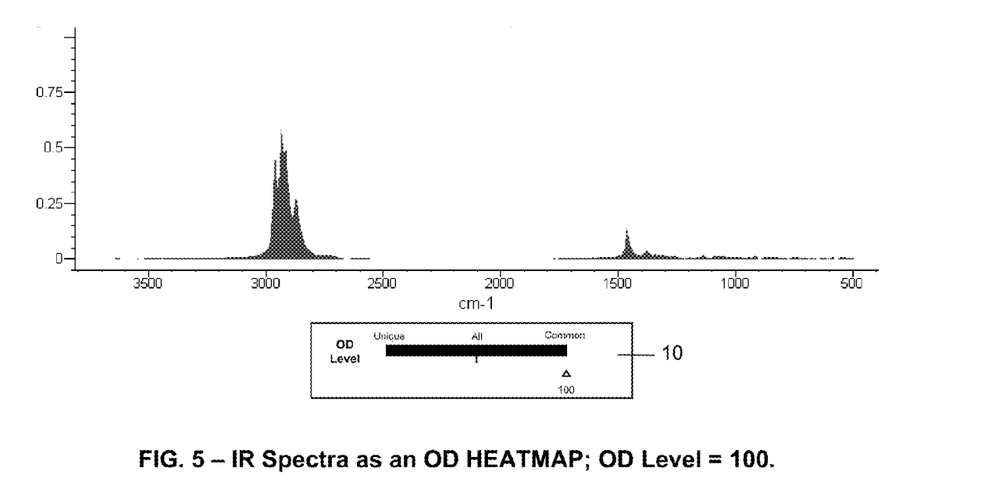
FIG. 5 illustrates a display of the IR spectra shown in FIG. 1 as an OD HEATMAP with the OD Scale value set to 100.

FIG. 5 shows the display of the IR spectra shown in FIG. 1 as an OD HEATMAP display with the OD scale value set to 100. With the OD scale set to 100, only those areas of the spectra that are present in all OBJECTS in the set of objects compared are displayed. In other words, only those values that appeared as pure red in FIG. 4 are displayed in FIG. 5. FIG. 5 clearly shows the areas common to all spectra in the set.

Figure 6:
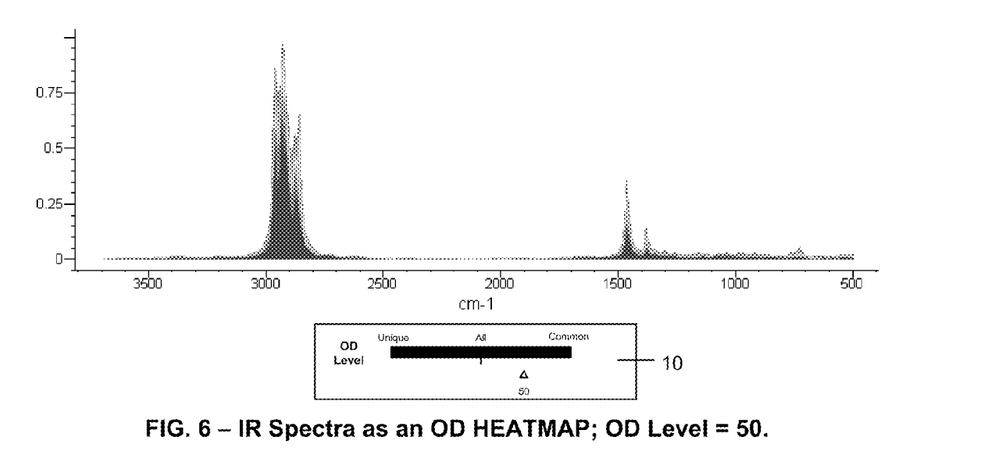
FIG. 6 illustrates a display of the IR spectra shown in FIG. 1 as an OD HEATMAP with the OD Scale value set to 50.

FIG. 6 shows the display of the IR spectra shown in FIG. 1 as an OD HEATMAP display with the OD scale value set to 50. With the OD scale set to 50, the areas of the IR spectra where 50% or more of the spectral regions are overlapping are displayed. That is, areas of the IR spectra occurrence count array with an $M/M_{max}$ value greater than or equal to 0.5 are displayed. FIG. 6 clearly shows the most common areas in the spectral set.

Figure 7:
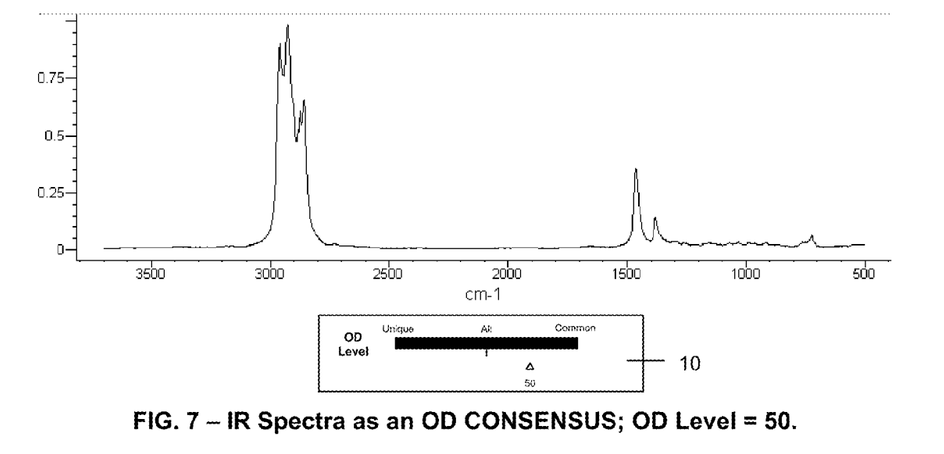
FIG. 7 illustrates a display of the IR spectra shown in FIG. 1 as an OD CONSENSUS representing a single consensus IR spectrum of the maximal value of all spectral regions where the OD Scale value=50, i.e., where 50% of the spectral OBJECTS overlap.

FIG. 7 shows an OD CONSENSUS display representing a single consensus IR spectrum of the maximal value of all spectral regions where the OD scale value=50, i.e., where 50% of the spectral OBJECTS overlap. This corresponds to the maximal values of the HEATMAP OBJECT displayed in FIG. 6.

Figure 8:
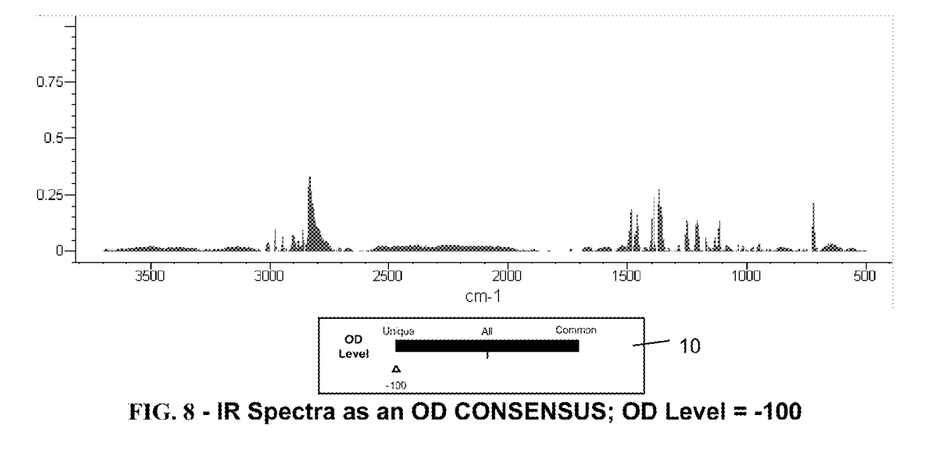
FIG. 8 illustrates a display of the IR spectra shown in FIG. 1 as an OD HEATMAP with the OD Scale set to −100.

FIG. 8 shows the display of the IR spectra shown in FIG. 1 as an OD CONSENSUS display with the OD scale value set to −100. With the OD scale set to −100, the areas of the IR spectra where 0% of the spectral regions are overlapping are displayed. That is, unique data with no overlap (UNION MINUS ALL INTERSECTIONS; $(M/N)_{min}$) is displayed.

In one aspect, a user is able to graphically adjust the OD scale value to any value between I and J, e.g., any decimal between −100 and 0, and between J and K, e.g., any decimal between 0 and 100. For example, this may be done in real-time by a user interacting with a graphical slider at the right of the display, e.g., using a mouse, keyboard or other selection device to interact with the slider 10 shown in FIG. 9 and at the bottom in FIGS. 4-8. As shown, slider 10 allows a user to select among and in between "Common," "ALL" and "Unique" levels. In one aspect, the "All" level displays the entire OD Heatmap for all OD levels. Selection of the "Common," level, in one aspect, displays only those areas that are common to 100% of the objects, that is, those objects with the highest OD levels. Moving the slider up to the "Common," level of the scale will remove more and more of the information of the lowest OD levels. Selection of the "Unique" level displays only those areas that are completely unique and have nothing in common with any other object, that is, those objects with the lowest OD levels. Moving the slider down to "Unique" will remove more and more of the information of the highest OD levels. For example, for the IR spectra displayed in FIG. 1, if a user selects "Common," from slider 10, a display similar to FIG. 5 would be displayed (INTERSECTION). Similarly, if a user selects "ALL" from slider 10, a display similar to FIG. 4 would be displayed (UNION). If a user selects "Unique" from slider 10, a display similar to FIG. 8 would be displayed (OD DIFFERENCE; UNION MINUS ALL INTERSECTIONS; $(M/N)_{min}$).

An example of code configured to perform the operations 130 and 140 on an input array of spectral (2-dimensional) vectors of x-y values using the J to K slider portion of display slider 10 shown in FIGS. 4-7 according to one aspect is shown below:

```
// Input: array of spectral vectors, all normalized to contain X number
of data points
// heatmap_array: allocated to contain X*Y elements, where Y depends
on the resolution of the input vectors (256 or 1024).
// spectrum_vector: input array of data vectors, normalized from 0 to 1
// Calculate heatmap array (occurrence count)
for int x=1 to X
    for int y=1 to Y
        heatmap_array[x][y]=0
    end for
end for
for int i=1 to number_of_vectors
    for int x=1 to X
        for int y=1 to spectrum_vector[i][x]*Y
            heatmap_array[x][y]+=1
        end for
    end for
end for
// Calculate maximum heatmap value for normalization
int max_val=0
for int x=1 to X
    for int y=1 to Y
        if heatmap_array[x][y]>max_val then
            max_val=heatmap_array[x][y]
    end for
end for
// Color gradient array
COLOR colors[NUM_COLS]
// cutoff: threshold value above which a heatmap pixel will be drawn
(ranges from 0 to 1)
// Draw picture
for int x=1 to X
    for int y=1 to Y
        if heatmap_array[x][y]/max_val>cutoff then
            DrawPixel(x, y,
                colors[heatmap_array[x][y]*(NUM_COLS-1)/max_val])
    end for
end for
// Generate a normalized consensus spectrum
int consensusVector[X]
for int x=1 to X
    consensusVector[x]=0
    for int y=Y to 1 step −1
        if heatmap_array[x][y]/max_val>cutoff then
            consensusVector[x]=y−1
```

-continued

```
            break for
        end if
    end for
end for
```

According to another aspect, for an input array of spectral (3-dimensional) vectors of x-y-z values, where a heatmap array is allocated to contains X*Y*Z elements, parts of the code above might look like:

```
// Calculate heatmap array
for int x=1 to X
    for int y=1 to Y
        for int z=1 to Z
            heatmap_array[x][y][z]=0
        end for
    end for
end for
for int i=1 to number_of_vectors
    for int x=1 to X
        for int y=1 to Y
            for int z=1 to spectrum_vector[i][x][y]*Z
                heatmap_array[x][y][z]+=1
            end for
        end for
    end for
end for
// Calculate maximum heatmap value for normalization
int max_val=0
for int x=1 to X
    for int y=1 to Y
        for int z=1 to Z
            if heatmap_array[x][y][z]>max_val then
                max_val=heatmap_array[x][y][z]
            end if
        end for
    end for
end for
```

In this aspect, 3-dimensional graphical OD HEATMAP and OD CONSENSUS displays may be generated or rendered, or 2-dimensional displays may be generated by selecting the appropriate X-Y, X-Z or Y-Z heatmap array elements (e.g., setting z, y or x to a specific value).

Figure 9:
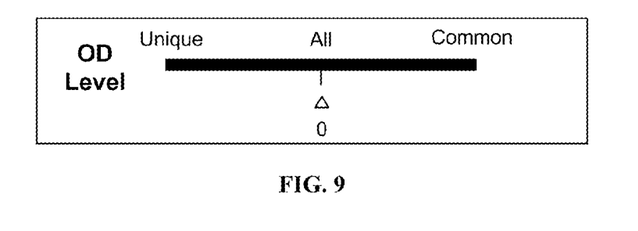
FIG. 9 shows a slider bar that allows a user to select different display types and parameters according to one aspect.
Figure 10:
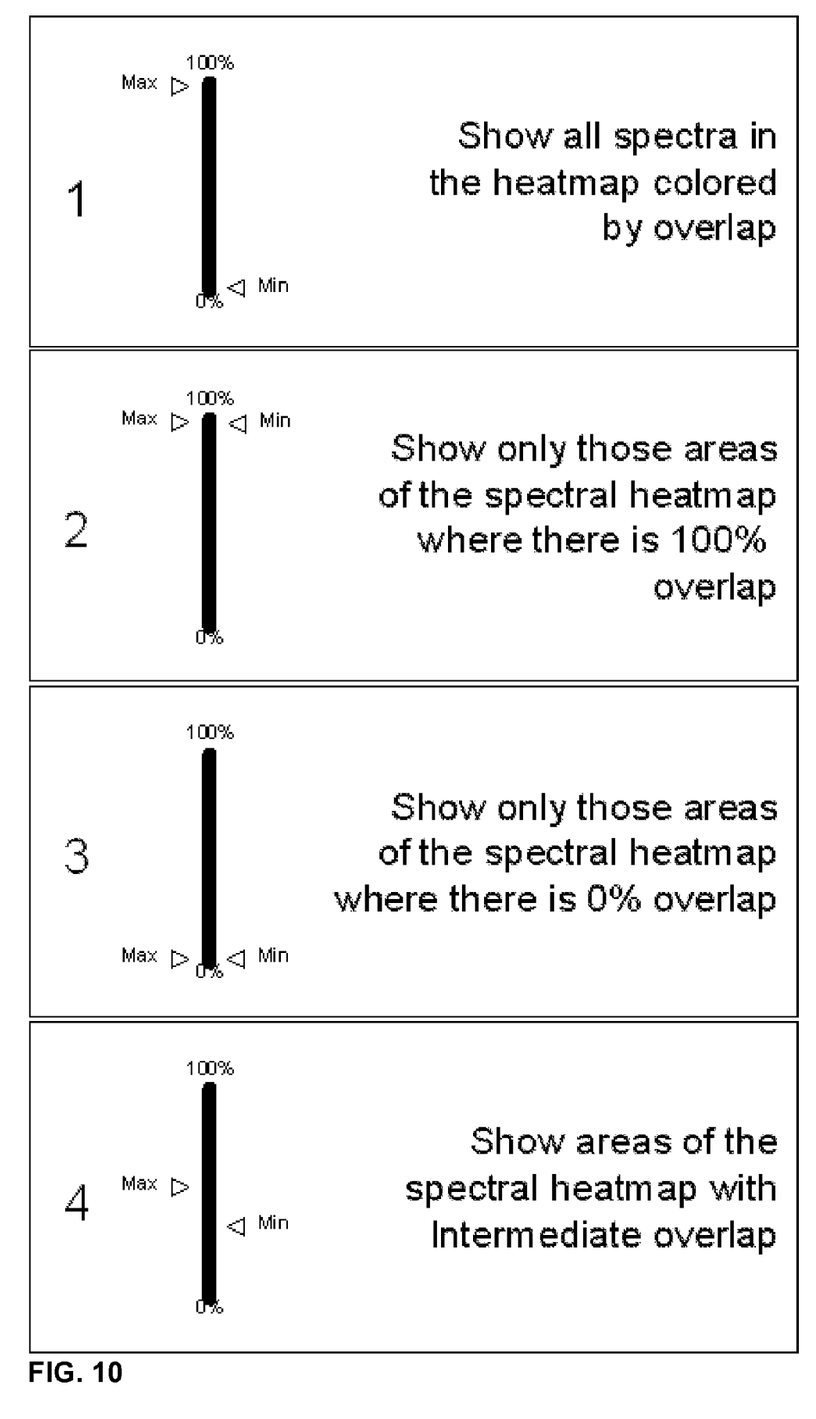
FIG. 10 shows a slider bar with individual slider arms to allow a user to select both minimum (Min) and maximum (Max) cutoff levels according to one aspect.

An example of code configured to generate a display and generate a normalized consensus spectrum for use with the entire display slider 10 shown in FIG. 9, according to one aspect, is shown below:

```
// minCutoff: threshold value above which a heatmap pixel will be drawn
(may range from 0 to maxCutoff)
// maxCutoff: threshold value below which a heatmap pixel will be drawn
(may range from minCutoff to 1)
// Draw picture
for int x=1 to X
    int yDraw=1;
    for int y=1 to Y
        double val= heatmap_array[x][y]/max_val
        if val>minCutoff AND val<=maxCutoff then
            DrawPixel(x, yDraw,
                colors[heatmap_array[x][y]*(NUM_COLS-1)/max_val])
            yDraw+=1
        end if
    end for
end for
// Generate a normalized consensus spectrum
int consensusVector[X]
for int x=1 to X
    consensusVector[x]=0
```

-continued

```
    int maxY=Y
    for int y=1 to Y
        if heatmap_array[x][y]/max_val<=maxCutoff then
            maxY=y
            break for
        end if
    end for
    for int y=Y to 1 step -1
        if heatmap_array[x][y]/max_val>minCutoff then
            consensusVector[x]=y-maxY
            break for
        end if
    end for
end for
```

Similarly, an example of code for generating a normalized consensus surface for 3-dimensional vectors might look like:

```
// Generate a normalized consensus surface area
int consensusSurface[X][Y]
for int x=1 to X
    for int y=1 to Y
        consensusSurface[x][y]=0
        int maxZ=Z
        for int z=1 to Z
            if heatmap_array[x][y][z]/max_val<=maxCutoff then
                maxZ=z
                break for
            end if
        end for
        for int z=Z to 1 step -1
            if heatmap_array[x][y][z]/max_val>minCutoff then
                consensusSurface[x][y]=z-maxZ
                break for
            end if
        end for
    end for
end for
```

According to yet another aspect, as shown in FIG. 10, a slider bar with individual slider arms for both minimum (Min) and maximum (Max) levels is provided. For the above code, the "Min" and "Max" slider arms allow a user to select the "MinCutoff" and "MaxCutoff" values. For example, for the IR spectra displayed in FIG. 1, if a user selects the configuration shown in FIG. 10(1), a display similar to FIG. 4 would be displayed (UNION). Similarly, if a user selects the configuration shown in FIG. 10(2), a display similar to FIG. 5 would be displayed (INTERSECTION). If a user selects the configuration shown in FIG. 10(3), a display similar to FIG. 8 would be displayed (UNION MINUS ALL INTERSECTIONS) Selection of intermediate values of "MinCutoff" and "MaxCutoff" would produce displays for the selected range of overlap. With reference back to FIGS. 4-9, it is understood that slider 10 is configured to allow a user to adjust the "MinCutoff" value with the "MaxCutoff" value set at 100 (or 100%).

It should be appreciated that the processes of the present invention, or portions thereof, may be implemented in computer code running on a processor of a computer system. The code includes instructions for controlling a processor or multiple processors to implement various aspects and steps of process 100. The code is typically stored on a hard disk, ROM, RAM or portable medium such as a CD, DVD, etc. Similarly, the process 100, or portions thereof, may be implemented in a data acquisition device including a processor executing instructions stored in a memory unit coupled to the processor. Portions or all of the code including such instructions may be embodied in a carrier signal which may be transmitted or downloaded to the data acquisition device memory unit over a wired and/or wireless network connection or direct connection to a code source, or may otherwise be provided using a portable medium as is well known. In certain aspects, the processes of the present invention can be coded using a variety of programming languages such as C, C++, C#, Fortran, Visual Basic®, etc., as well as applications such as Mathematica® which may provide pre-packaged routines, functions and procedures useful for data visualization and analysis. Another example of the latter is MATLAB®.

The OD display systems and methods of the present invention can be directly applied in various scientific and statistical fields of endeavor. For example, in the field of metabolomics, the OD display systems and methods allow researchers to automatically create a biomarker for each disease state classified in a statistical analysis by using an OD CONSENSUS from the collected spectra or chromatograms resulting from each disease state classified in the statistical analysis. The resulting OD CONSENSUS spectra or chromatograms allow researchers to diagnose a disease state by comparing unknown spectra or chromatograms directly against the standard set by the OD CONSENSUS spectra or chromatograms. OD DIFFERENCE displays are also useful, for example in the field of metabolomics.

While the invention has been described by way of example and in terms of the specific embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A machine-implemented method of displaying a plurality of similar data sets, the method comprising:
   receiving into a processor a plurality of N data sets, each data set including two or more data points, each data point having 2 or more data values representing a vector having a number of dimensions;
   generating an occurrence count array including elements by determining an occurrence count value, M, for each array element, wherein each occurrence count value, M, is a number of times a corresponding data point occurs in the plurality of N data sets, wherein each array element corresponds to a discrete interval of data values;
   receiving an indicator of overlap density, said indicator identifying a degree of overlap;
   determining the array elements that are within the identified degree of overlap; and
   generating graphical data for a graphical display representing said elements in the array that are within the identified degree of overlap,
   wherein N is an integer greater than or equal to two and M is an integer greater than or equal to zero.

2. The method of claim 1 wherein the number of dimensions is 3.

3. The method of claim 1, wherein the graphical display is an overlap density HEATMAP display representing all elements in the array having the identified degree of overlap, wherein elements having different ranges of occurrence count values are displayed in a format selected from the group consisting of different colors, shades and patterns.

4. The method of claim 3, wherein the indicator identifies a degree of commonality range of between 0 and 1, and wherein the display represents a union of between 2 and all N data sets.

5. The method of claim 3, wherein the indicator identifies a degree of commonality equal to 1, and wherein the display represents an intersection of all N data sets.

6. The method of claim 3, wherein the indicator identifies a degree of commonality equal to 0, and wherein the display represents a difference of all N data sets.

7. The method of claim 1, wherein the graphical display is an overlap density CONSENSUS display representing the maximal value across all elements in the array having the identified degree of overlap.

8. The method of claim 1, wherein determining includes:
   determining a maximum occurrence count value $M_{max}$ for the entire array, where $0<M_{max}\leq N$; and
   for each array element, comparing the indicator with $M/M_{max}$ to determine whether that element is within the identified degree of overlap.

9. The method of claim 1, wherein the received indicator includes a minimum value and a maximum value.

10. The method of claim 1 wherein the processor is coupled to a data acquisition device.

11. A machine-readable storage medium storing code for controlling a processor to generate graphical data for rendering a display of a plurality of similar data sets, the code including instructions to:
   generate an occurrence count array for a plurality of N data sets, each data set including two or more data points, each data point having 2 or more data values representing a vector having a number of dimensions, the array including elements, by determining an occurrence count value, M, for each array element, wherein each occurrence count value, M, is a number of times a corresponding data point occurs in the plurality of N data sets, wherein each array element corresponds to a discrete interval of data values;
   determine the array elements that are within an identified degree of overlap responsive to a user input indicator of overlap density; and
   generate graphical data for a graphical display representing said elements in the array that are within the identified degree of overlap,
   wherein N is an integer greater than or equal to two and M is an integer greater than or equal to zero.

12. The machine-readable storage medium of claim 11, wherein the indicator identifies a degree of commonality range of between 0 and 1, and wherein the display represents a union of between 2 and all N data sets.

13. The machine-readable storage medium of claim 11, wherein the indicator identifies a degree of commonality equal to 1, and wherein the display represents an intersection of all N data sets.

14. The machine-readable storage medium of claim 11, wherein the indicator identifies a degree of commonality equal to 0, and wherein the display represents unique values throughout all N data sets.

15. The machine-readable storage medium of claim 11, wherein the graphical display is an overlap density CONSENSUS display representing the maximal value across all elements in the array having the identified degree of overlap.

16. The machine-readable storage medium of claim 11, wherein the graphical display is an overlap density HEATMAP display representing all elements in the array having the identified degree of overlap, wherein elements having different ranges of occurrence count values are displayed in a format selected from the group consisting of different colors, shades and patterns.

17. The machine-readable storage medium of claim 11, wherein the instructions to determine include instructions to:

> determine a maximum occurrence count value $M_{max}$ for the entire array, where $0 < M_{max} \leq N$; and
>
> > for each array element, compare the indicator with $M/M_{max}$ to determine whether that element is within the identified degree of overlap.

18. A system for generating graphical data for rendering a display of a plurality of similar data sets, the system comprising:

> a processor configured to generate an occurrence count array for a plurality of N data sets, each data set including two or more data points, each data point having 2 or more data values representing a vector having a number of dimensions, the array including elements, by determining an occurrence count value, M, for each array element, wherein each occurrence count value, M, is a number of times a corresponding data point occurs in the plurality of N data sets, wherein each array element corresponds to a discrete interval of data values;
>
> the processor further configured to determine the array elements that are within an identified degree of overlap responsive to a user input indicator of overlap density; and
>
> the processor further configured to generate graphical data for a graphical display representing said elements in the array that are within the identified degree of overlap,
>
> wherein N is an integer greater than or equal to two and M is an integer greater than or equal to zero.

19. The system of claim 18 further comprising a data acquisition device.

20. The system of claim 18 wherein the number of dimensions is 3, and further comprising a graphical display upon which the graphical data is displayed representing 3 dimensions.

* * * * *